(12) United States Patent
Okuhara

(10) Patent No.: US 7,531,690 B2
(45) Date of Patent: May 12, 2009

(54) PALLADIUM, TUNGSTEN AND ZIRCONIUM-BASED CATALYST FOR PRODUCTION OF OXYGEN-CONTAINING COMPOUND, PRODUCTION PROCESS OF THE CATALYST, AND PRODUCTION PROCESS OF OXYGEN-CONTAINING COMPOUND USING THE CATALYST

(75) Inventor: Toshio Okuhara, Sapporo (JP)

(73) Assignee: Showa Denko K.K., Tokyo (JP)

( * ) Notice: Subject to any disclaimer, the term of this patent is extended or adjusted under 35 U.S.C. 154(b) by 300 days.

(21) Appl. No.: 10/592,007

(22) PCT Filed: Mar. 28, 2005

(86) PCT No.: PCT/JP2005/006528

§ 371 (c)(1),
(2), (4) Date: Sep. 7, 2006

(87) PCT Pub. No.: WO2005/092445

PCT Pub. Date: Oct. 6, 2005

(65) Prior Publication Data

US 2007/0191224 A1 Aug. 16, 2007

Related U.S. Application Data

(60) Provisional application No. 60/558,557, filed on Apr. 2, 2004.

(30) Foreign Application Priority Data

Mar. 29, 2004 (JP) ............................. 2004-094060

(51) Int. Cl.
| | |
|---|---|
| B01J 21/06 | (2006.01) |
| B01J 23/30 | (2006.01) |
| B01J 23/44 | (2006.01) |
| B01J 23/652 | (2006.01) |
| B01J 37/02 | (2006.01) |
| B01J 37/03 | (2006.01) |
| B01J 37/08 | (2006.01) |
| C01G 25/02 | (2006.01) |
| C01G 41/00 | (2006.01) |
| C01G 41/02 | (2006.01) |
| C01G 55/00 | (2006.01) |
| C01G 1/02 | (2006.01) |
| C07C 49/08 | (2006.01) |
| C07C 49/10 | (2006.01) |
| C07C 51/16 | (2006.01) |

(52) U.S. Cl. ................... 562/548; 562/544; 502/308; 502/313; 502/325; 502/339; 502/349; 423/22; 423/53; 423/54; 423/594.12; 423/594.13; 423/606; 423/608

(58) Field of Classification Search ............ 502/308, 502/313, 325, 339, 349; 423/22, 53, 54, 423/594.12, 594.13, 606, 608; 562/544, 562/548
See application file for complete search history.

(56) References Cited

U.S. PATENT DOCUMENTS

| | | | |
|---|---|---|---|
| 3,459,796 | A | 8/1969 | Duncanson et al. |
| 3,970,697 | A | 7/1976 | Scheben et al. |
| 5,405,996 | A | 4/1995 | Suzuki et al. |
| 5,902,767 | A * | 5/1999 | Kresge et al. ............... 502/308 |
| 6,274,765 | B1 | 8/2001 | Borchert et al. |
| 6,399,816 | B1 | 6/2002 | Borchert et al. |
| 2004/0013592 | A1 | 1/2004 | Ohtsuka et al. |

FOREIGN PATENT DOCUMENTS

| | | |
|---|---|---|
| EP | 0 294 845 A1 | 12/1988 |
| EP | 0 407 091 A1 | 1/1991 |
| EP | 0 620 205 A1 | 10/1994 |
| EP | 1063010 A1 * | 12/2000 |
| FR | 1448361 | 8/1965 |
| FR | 2 841 797 A1 | 1/2004 |
| JP | 46-006763 | 2/1971 |
| JP | 47-013221 | 7/1972 |
| JP | 51-029425 | 3/1976 |
| JP | 54-57488 A | 5/1979 |
| JP | 6-293695 A | 10/1994 |
| JP | 7-89896 A | 4/1995 |
| JP | 9-67298 A | 3/1997 |
| WO | WO 95/03121 A1 | 2/1995 |
| WO | WO 98/47850 A1 | 10/1998 |
| WO | WO 99/20592 A1 | 4/1999 |
| WO | WO 00/00284 A2 | 1/2000 |

OTHER PUBLICATIONS

Patent Abstracts of Japan, vol. 1995, No. 01, Feb. 28, 1995, and JP 06 293695 A, (Showa Denko KK), Oct. 21, 1994, Abstract.

* cited by examiner

*Primary Examiner*—Timothy C Vanoy
*Assistant Examiner*—Serena L Hanor
(74) *Attorney, Agent, or Firm*—Sughrue Mion, PLLC

(57) ABSTRACT

A catalyst for the production of an oxygen-containing compound, comprising palladium, tungsten and zirconium, a production process thereof, and a production process of an oxygen-containing compound using the catalyst. The catalyst can provide an oxygen-containing compound from a lower olefin and oxygen with high productivity and high selectivity.

5 Claims, No Drawings

PALLADIUM, TUNGSTEN AND ZIRCONIUM-BASED CATALYST FOR PRODUCTION OF OXYGEN-CONTAINING COMPOUND, PRODUCTION PROCESS OF THE CATALYST, AND PRODUCTION PROCESS OF OXYGEN-CONTAINING COMPOUND USING THE CATALYST

This application claims the priority of application based on U.S. Provisional Application Ser. No. 60/558,557 (filed on Apr. 2, 2004).

TECHNICAL FIELD

The present invention relates to a catalyst for the production of an oxygen-containing compound, which is used for producing an oxygen-containing compound from an olefin and oxygen in a gas phase, a production process of the catalyst, and a production process of an oxygen-containing compound using the catalyst.

More specifically, the present invention relates to a novel catalyst for the production of an oxygen-containing compound (for example, acetic acid), comprising tungsten, zirconium and palladium, a production process of the catalyst, and a production process of an oxygen-containing compound using the catalyst.

BACKGROUND ART

Many studies have been heretofore made on the method of obtaining an oxygen-containing compound from an olefin and oxygen.

In particular, with respect to the catalyst of producing acetic acid from ethylene and oxygen through one stage, for example, a liquid phase one-stage oxidation process using an oxidation-reduction catalyst comprising a metal ion pair such as palladium-cobalt and palladium-iron (see, Patent Document 1 (French Patent No. 1,448,361)), a process using a catalyst comprising a palladium-phosphoric acid or a sulfur-containing modifying agent (Patent Document 2 (Japanese Unexamined Patent Publication (Kokai) No. 47-013221) and Patent Document 3 (Kokai No. 51-029425)), and a gas phase one-stage oxidation process using a catalyst comprising a 3 group-type oxygen compound (see, Patent Document 4 (Kokoku No. 46-006763)) have been proposed.

Also, with respect to the process of producing acetic acid by using a catalyst containing a palladium compound and a heteropolyacid, for example, a gas phase one-stage oxidation process using a catalyst comprising palladium phosphovanadomolybdate has been proposed (see, Patent Document 5 (Kokai No. 54-57488)).

Further, a catalyst containing at least one compound selected from the group consisting of palladium, heteropolyacids and salts thereof is disclosed as a catalyst of ensuring higher productivity and selectivity than those of the above-described various catalysts (see, Patent Document 6 (Kokai No. 7-89896) and Patent Document 7 (Kokai No. 9-67298)).

These catalysts comprising palladium and a heteropolyacid have a sufficiently high performance in industrially producing acetic acid from ethylene and oxygen. However, the heteropolyacid is low in the thermal stability, specifically, unstable at a temperature of 400° C. or more, and therefore, requires care in view of stable operation. In addition, it is difficult to perform firing at a high temperature for the reclamation of catalyst.

On the other hand, a composite oxide catalyst has been reported as a catalyst of producing acetic acid from ethylene and oxygen. This composite oxide is characterized by having relatively high heat resistance as compared with heteropolyacids.

EP-A-294,845 (Patent Document 8) discloses a process for selectively producing acetic acid from ethane, ethylene or a mixture thereof and oxygen in the presence of a catalyst mixture containing:

A) a calcined catalyst represented by the formula:

$Mo_xV_y$ or $Mo_xV_yY_z$

[wherein Y can be one or more metals of Li, Na, Be, Mg, Ca, Sr, Ba, Zn, Cd, Hg, Sc, Y, La, Ce, Al, Ti, Lr, Hf, Pb, N b, Ta, As, Sb, Bi, Cr, W, U, Te, Fe, Co and Ni, x is 0.5 to 0.9, y is 0.1 to 0.4, and z is 0.001 to 1], and B) an ethylene hydration catalyst and/or an ethylene oxidation catalyst. The second catalyst component B is suitably a molecular sieve catalyst or a palladium-containing catalyst, and high performance cannot be obtained by a catalyst containing the component A or B alone.

EP-A-407,091 (Patent Document 9) discloses a process for producing a mixture comprising ethylene and/or acetic acid. In this case, a gas containing ethane and/or ethylene and molecular oxygen is brought into contact with a catalyst composition containing elements A, X and Y at a high temperature, where A is $Mo_dRe_eW_f$ (wherein d and f each is 0 or more, e is more than 0, and d+e+f=1), X is Cr, Mn, Nb, Ta, Ti, V and/or W, and Y is Bi, Ce, Co, Cu, Fe, K, Mg, Ni, P, Pb, Sb, Si, Sn, Tl and/or U.

International Publication No. 99/20592 (Patent Document 10), pamphlet, discloses a process of selectively producing acetic acid in a high temperature region from ethane, ethylene or a mixture thereof and oxygen in the presence of a catalyst represented by the formula:

$Mo_aPd_bX_cY_d$

[wherein X represents one or multiple members of Cr, Mn, Nb, Ta, Ti, V, Te and W; Y represents one or multiple members of B, Al, Ga, In, Pt, Zn, Cd, Bi, Ce, Co, Rh, Ir, Cu, Ag, Au, Fe, Ru, Os, K, Rb, Cs, Mg, Ca, Sr, Ba, Nb, Zr, Hf, Ni, P, Pb, Sb, Si, Sn, Tl and U; a=1, b=0.0001 to 0.01, c=0.4 to 1, and d=0.005 to 1].

International Publication No. 00/00284, pamphlet (Patent Document 11) discloses MoVNbPd or MoVLaPd as the catalyst for obtaining acetic acid from ethylene and oxygen.

With respect to the catalyst containing tungsten and noble metal, International Publication No. 98/47850 (Patent Document 12), pamphlet, discloses a production process of acetic acid from ethane, ethylene or a mixture thereof, and also discloses a catalyst represented by the formula:

$W_aX_bY_cZ_d$

[wherein X represents one or multiple members of Pd, Pt, Ag and Au, Y represents one or multiple members of V, Nb, Cr, Mn, Fe, Sn, Sb, Cu, Zn, U, Ni and Bi, Z represents one or multiple members of Li, Na, K, Rb, Cs, Be, Mg, Ca, Sr, Ba, Sc, Y, La, Ti, Zr, Hf, Ru, Os, Co, Rh, Ir, B, Al, Ga, In, Tl, Si, Ge, Pb, P, As and Te, a=1, b>0, c>0 and d=0 to 2]. But, this patent publication is silent on the reactivity when ethylene is used as the raw material, and moreover, sufficiently high performance is not obtained.

In this International Publication No. 98/47850 (Patent Document 12), pamphlet, it is stated that since the catalyst containing molybdenum disadvantageously produces a volatile molybdenum compound under the reaction conditions and the compound produced decreases the activity of catalyst and the selectivity, a catalyst system mainly comprising more stable tungsten is proposed.

However, International Publication No. 98/47850 (Patent Document 12), pamphlet, sets forth no working example using ethylene as a raw material. This catalyst system is presumed to have high oxidation activity so as to activate ethane low in the reactivity and therefore, when a large amount of ethylene having high reactivity is introduced, there may arise an overreaction such as polymerization or combustion reaction of ethylene. In any case, the catalyst described in this patent publication cannot be understood as an optimal catalyst system in the case of using ethylene as a raw material.

[Patent Document 1] French Patent 1,448,361
[Patent Document 2] Kokai No. 47-013221
[Patent Document 3] Kokai No. 51-029425
[Patent Document 4] Kokoku No. 46-006763
[Patent Document 5] Kokai No. 54-57488
[Patent Document 6] Kokai No. 7-89896
[Patent Document 7] Kokai No. 9-67298
[Patent Document 8] EP-A-294,845
[Patent Document 9] EP-A-407,091
[Patent Document 10] International Publication No. 99/20592, pamphlet
[Patent Document 11] International Publication No. 00/00284, pamphlet
[Patent Document 12] International Publication No. 98/47850, pamphlet

DISCLOSURE OF INVENTION

One object of the present invention is to provide a novel and high-performance catalyst which can make it possible to produce an oxygen-containing compound from an olefin and oxygen (particularly, to produce acetic acid from ethylene and oxygen).

Another object of the present invention is to provide a process for producing the above-described catalyst for the production of an oxygen-containing compound.

Still another object of the present invention is to provide a production process of an oxygen-containing compound using the catalyst.

As a result of intensive investigations, the present inventors have found that, surprisingly, a catalyst comprising tungsten, zirconium and palladium can be a catalyst usable in obtaining an oxygen-containing compound from an olefin and oxygen (particularly, a catalyst which can make it possible to obtain acetic acid from ethylene and oxygen with high productivity and high selectivity). The present invention has been accomplished based on this finding.

That is, the present invention (I) is a catalyst for the production of an oxygen-containing compound, which is used for a process of producing acetic acid by reacting ethylene and oxygen molecule in a gas phase, the catalyst being represented by the following formula:

$Pd/W_aZrO_x$

[wherein Pd means a palladium-containing compound, a is a W/Zr molar ratio, and x is a value defined by the oxidized state of tungsten (W), zirconium (Zr) and palladium (Pd)].

The present invention (II) is a process for producing the catalyst for the production of an oxygen-containing compound of the present invention (I).

The present invention (III) is a process for producing acetic acid by using the catalyst for the production of an oxygen-containing compound of the present invention (I).

Further, the present invention includes, for example, the following embodiments.

[1] A catalyst for the production of an oxygen-containing compound, which is used for a process of producing an oxygen-containing compound by reacting an olefin and oxygen, said catalyst being represented by the following formula:

$Pd/W_aZrO_x$

[wherein Pd means a palladium-containing compound, a is a W/Zr molar ratio, and x is a value defined by the oxidized state of tungsten (W), zirconium (Zr) and palladium (Pd)].

[2] The catalyst for the production of an oxygen-containing compound according to [1], wherein the content of palladium element in said catalyst is from 0.001 to 15 parts based on 100 parts of $W_aZrO_x$ and the W/Zr molar ratio is from 0.01 to 5.0.

[3] The catalyst for the production of an oxygen-containing compound according to [1] or [2], wherein said olefin is ethylene and said oxygen-containing compound is acetic acid.

[4] The catalyst for the production of an oxygen-containing compound according to [1] or [2], wherein said olefin is propylene and said oxygen-containing compound is at least one compound selected from acetone, propionaldehyde, propionic acid and acetic acid.

[5] The catalyst for the production of an oxygen-containing compound according to [1] or [2], wherein said olefin is at least one member selected from 1-butene, cis-2-butene and trans-2-butene, and said oxygen-containing compound is at least one compound selected from methyl ethyl ketone, n-butylaldehyde, butyric acid, propionaldehyde, propionic acid, acetaldehyde and acetic acid.

[6] A process for producing a catalyst for the production of an oxygen-containing compound, which is a process of producing the catalyst for the production of an oxygen-containing compound according to any one of [1] to [5], said process comprising the following first and second steps:

First Step:

a step of causing a tungsten compound and a zirconium compound to coexist and heat-treating these compounds to produce a compound represented by the following formula:

$W_aZrO_y$

[wherein a is a W/Zr molar ratio, and y is a value defined by the oxidized state of tungsten (W), and zirconium (Zr)];

Second Step:

a step of loading palladium compound on the compound $W_aZrO_y$ obtained in the first step to obtain a catalyst for the production of an oxygen-containing compound.

[7] The process for producing a catalyst for the production of an oxygen-containing compound according to [6], wherein in said first step, the heat-treatment temperature is from 400 to 1,200° C.

[8] A process for producing an oxygen-containing compound, comprising reacting an olefin and oxygen in a gas phase in the presence of the catalyst for the production of an oxygen-containing compound according to any one of [1] to [5].

[9] A process for producing acetic acid, comprising reacting ethylene and oxygen in a gas phase in the presence of the catalyst for the production of an oxygen-containing compound according to any one of [1] to [5].

BEST MODE FOR CARRYING OUT THE INVENTION

The present invention is described in detail below. In the following, unless otherwise indicated, the "parts" and "%" showing a quantitative ratio are on the mass basis.

(Present Invention (I): Catalyst for Production of Oxygen-Containing Compound)

The present invention (I) is described below. The present invention (I) is a catalyst for the production of an oxygen-containing compound, which is used for a process of producing acetic acid by reacting an olefin, particularly ethylene, and oxygen molecule in a gas phase, the catalyst being represented by the formula:

$$Pd/W_aZrO_x$$

[wherein Pd means a palladium-containing compound, a is a W/Zr molar ratio, and x is a value defined by the oxidized state of tungsten (W), zirconium (Zr) and palladium (Pd)].

The olefin as used in the present invention is a compound having a carbon-carbon double bond, such as ethylene, propylene, butenes, butadiene, pentenes and hexenes. Among these, the olefin is preferably ethylene or propylene, more preferably ethylene.

As for the constituent components of the catalyst for the production of an oxygen-containing compound of the present invention (I), palladium, tungsten, zirconium and oxygen are essential components.

In the catalyst for the production of an oxygen-containing compound of the present invention (I), an arbitrary element may be added, if desired.

(Palladium Compound)

The palladium compound for use in the present invention (I) may be in any state, for example, may be a compound or the element as-is, that is, may be in an ionic state or in a zero valence state, so-called metal state.

The palladium element concentration in the catalyst is (based on 100 parts of $W_aZrO_x$) preferably from 0.001 to 15 parts, more preferably from 0.005 to 10 parts, still more preferably from 0.01 to 5 parts. If the palladium concentration is less than 0.001 parts, the productivity of acetic aid may decrease, whereas if the palladium concentration exceeds 15 parts, the cost may rise because this is an expensive noble metal.

(Tungsten)

The tungsten in the catalyst of the present invention (I) is preferably in an oxide state and the valence thereof is generally from 4 to 6.

(Zirconia)

The zirconia for use in the catalyst of the present invention (I) is preferably in an oxide state and the valence thereof is generally from 2 to 4.

(Tungsten-Zirconium)

The compositional ratio of constituent elements of tungsten-zirconium ($W_aZrO_y$) is not limited. In the formula, a is a W/Zr molar ratio, and y is a value defined by the oxidized state of tungsten, and zirconium. The tungsten/zirconium (W/Zr) ratio is preferably, in terms of the molar ratio, from 0.01 to 5, more preferably from 0.02 to 3, still more preferably from 0.05 to 1.

(Activity of Catalyst)

The high activity and role of the catalyst of the present invention (I) in the production of an oxygen-containing compound (for example, acetic acid) are not particularly elucidated but according to the knowledge of the present inventors, these are presumed as follows.

An oxide comprising tungsten and zirconium is generally a superacid known as zirconium tungstate. On the other hand, palladium is generally known as an oxidation catalyst. Here, as clearly known from Examples and Comparatives described later, even when a catalyst comprising tungsten and zirconium is used, acetic acid is scarcely produced (Comparative Example 4).

When a catalyst comprising a combination of palladium and zirconium is used, a small amount of acetic acid is obtained, but the space time yield (hereinafter simply referred to as "STY") and selectivity are low (Comparative Example 3). Only when palladium and zirconium tungstate are present together, high STY and selectivity of acetic acid can be obtained. From this, it is considered that some interaction is present among palladium, tungsten and zirconium and by the effect of this interaction, acetic acid can be obtained with high activity and selectivity from ethylene and oxygen.

(Measurement of Component Ratio)

The component ratio of each element: palladium, tungsten and zirconia contained in the catalyst of the present invention (I) can be properly measured, for example, by the following method.

A fixed amount of the catalyst is ground by a mortar or the like to produce a uniform powder, this catalyst powder is added to an acid such as hydrofluoric acid or aqua regia and dissolved with stirring under heat to produce a uniform solution, the obtained solution is diluted with pure water to an appropriate concentration to produce a solution for analysis, and this solution is quantitatively analyzed by a high-frequency inductively coupled plasma emission spectrometer (hereinafter referred to as "ICP") (for example, SPS-1700, manufactured by Seiko Instruments Inc.). The precision of the analyzer can be easily corrected by a commercially available standard reagent for each element, and determination with reproducibility can be made. (Present Invention (II): process for producing catalyst for production of oxygen-containing compound)

The process for producing a catalyst for the production of an oxygen-containing compound of the present invention (I) is not particularly limited. That is, insofar as the above-described catalyst components can be incorporated into the catalyst, conventionally known methods such as impregnation, precipitation, co-precipitation and kneading may be employed.

In view of production process and production cost, the production process of the present invention (II) described below is particularly preferred. The production process of the present invention (II) is a process for producing the catalyst for the production of an oxygen-containing compound of the present invention (I).

The present invention (II) comprises the following steps:

First Step:

a step of causing a tungsten compound and a zirconium compound to coexist and heat-treating these compounds to produce a compound represented by the following formula:

$$W_aZrO_y$$

[wherein a is a W/Zr molar ratio, and y is a value defined by the oxidized state of tungsten (W), and zirconium (Zr)];

Second Step:

a step of loading palladium on the compound $W_aZrO_y$ obtained in the first step to obtain a catalyst for the production of an oxygen-containing compound.

(First Step of Present Invention (II))

The first step of the present invention (II) is a step of causing a tungsten compound and a zirconium compound to coexist and heat-treating these compounds to produce $W_aZrO_y$.

(Tungsten Compound)

The tungsten compound for use in the present invention (II) may be any tungsten compound. Specific examples thereof include tungstic acid, tungstate such as ammonium metatungstate and ammonium paratungstate, tungsten chloride, tungsten sulfate and alkoxy tungsten.

(Zirconium Compound)

The zirconium compound for use in the present invention (II) may be any zirconium compound. Specific examples thereof include zirconium halide, zirconium oxyhalide, zirconium oxynitrate, zirconium hydroxide, zirconium oxide, zirconium acetate and zirconium sulfate. Preferably, such a zirconium compound is zirconium hydroxide. Zirconium hydroxide may be obtained by hydrolyzing a zirconium compound with an weak alkali and then dried at a temperature from room temperature to 400° C.

(Suitable Production Process)

As for the process of obtaining $W_aZrO_y$, tungstic acid may be loaded on and contained in the zirconium hydroxide by immersion, spraying or the like, but the zirconium hydroxide obtained as above is preferably dispersed in an aqueous solution of water-soluble ammonium tungstate, dehydration-dried at 300° C. or less, and then fired at a predetermined temperature to obtain $W_aZrO_y$.

(Oxide of Zirconium and Tungsten)

When the oxide comprising zirconium and tungsten is fired, the catalytic activity can be more enhanced. The firing temperature is preferably from 400 to 1,200° C., more preferably from 500 to 1,000° C. If the firing temperature is less than 400° C., the bonding between zirconium oxide and tungstic acid cannot be satisfactorily formed and the activity may decrease, whereas if it exceeds 1,200° C., the surface area seriously decreases to fail in assuring a sufficiently large contact area with a reaction substrate and therefore, the activity of obtained catalyst may decrease.

The obtained oxide comprising tungsten and zirconium is used as the support of palladium compound in the second step of the present invention (II), and the shape of the above support is not particularly limited. Specific examples thereof include, but are not limited to, powder form, spherical form and pellet form. The oxide may also be positively ground into powder form and may be further shaped into tablet form, pillar form or the like. The above support for use in the present invention is not particularly limited in its particle size. In the case of using the catalyst for the reaction of olefin and oxygen in a fixed-bed tubular reactor, when the support is spherical, its particle diameter is preferably from 1 to 10 mm, more preferably from 2 to 8 mm. In the case of performing the reaction by packing the catalyst in the tubular reactor, if the particle diameter is less than 1 mm, a large pressure loss is generated during flow of a gas and the gas circulation may not be effectively performed, whereas if the particle diameter exceeds 10 mm, the reaction gas cannot diffuse into the inside of the catalyst and the catalytic reaction may not effectively proceed.

In this way, $W_aZrO_y$ can be obtained in the first step.

(Second Step of Present Invention (II))

The second step of the present invention (II) is a step of loading palladium compound on $W_aZrO_y$ obtained in the first step to obtain a catalyst ($Pd/W_aZrO_x$) for the production of an oxygen-containing compound. Herein, in general, x=y, but x may be different from y.

(Raw Material Compound of Palladium)

The raw material compound of palladium used in the second step of the present invention (II) is not particularly limited. Specific examples thereof include chlorides such as palladium chloride, organic acid salts such as palladium acetate, and nitrates such as palladium nitrate. Other examples include Pd complexes having, as a ligand, an organic compound such as acetylacetonate, nitrile and ammonium.

(Loading of Palladium Compound)

The method for loading a palladium compound on $W_aZrO_y$ obtained in the first step may be any method. Specific examples thereof include a method of dissolving the raw material compound in an appropriate solvent (e.g., water, acetone) or in an inorganic or organic acid (e.g., hydrochloric acid, nitric acid, acetic acid) or a solution thereof, and directly or indirectly loading the compound on the surface layer. As for the direct loading, for example, an impregnation method or a spray method may be used.

(Reduction Treatment of Supported Catalyst)

In case the palladium compound is palladium salt, in the second step of the present invention (II), the supported catalyst obtained may be reduced, whereby the palladium salt can be converted into metal palladium. The reduction treatment is preferably performed with a reducing agent, preferably a gaseous reducing agent under normal reduction conditions.

The reducing agent is not particularly limited but examples thereof include hydrogen, ethylene, methanol and CO, and hydrazine. Among these, hydrogen gas and ethylene are preferred, and hydrogen gas is more preferred.

In the case of performing the reduction treatment, the temperature at the treatment is not particularly limited, but the catalyst obtained in the second step of the present invention is preferably heated at 50 to 600° C., more preferably from 100 to 500° C.

The treatment pressure is not particularly limited but in view of equipment, a pressure of 0.0 MPa (gauge pressure) to 3.0 MPa (gauge pressure) is advantageous in practice. The treatment pressure is more preferably from 0.1 MPa (gauge pressure) to 1.5 MPa (gauge pressure).

In the case of passing a gaseous reducing agent, the reducing agent may be used in any concentration, and, if desired, nitrogen, carbon dioxide, rare gas or the like can be used as a diluent. Also, the reduction may be performed by allowing ethylene, hydrogen or the like to be present in the presence of vaporized water. Further, acetic acid may be produced from ethylene and oxygen by packing the catalyst prepared in the second of the present invention (II) into a reactor of the reaction system and after reducing it with ethylene, further introducing oxygen.

The mixed gas containing the gaseous reducing agent is preferably passed through the catalyst, in the standard state, at a space velocity (hereinafter referred to as "SV") of 10 to 15,000 hr$^{-1}$, more preferably from 100 to 8,000 hr$^{-1}$.

The treatment style is not particularly limited, but use of a fixed bed where the above-described catalyst is packed in a reaction tube having corrosion resistance is preferred and practically advantageous.

In this way, the catalyst for the production of an oxygen-containing compound (I) can be obtained.

(Process for Producing Oxygen-Containing Compound by Using Catalyst for Production of Oxygen-Containing Compound)

The present invention (III) is described below. The present invention (III) is a process for producing an oxygen-containing compound (for example, acetic acid) from an olefin (particularly, ethylene) and oxygen gas by using the catalyst of the present invention (I).

(Olefin)

The olefin as used in the present invention is a compound having a C-C double bond, such as ethylene, propylene, butenes, butadiene, pentenes and hexenes. Among these, the olefin is preferably ethylene or propylene, more preferably ethylene.

In the process for producing an oxygen-containing compound of the present invention (III), the reaction temperature at the time of reacting an olefin (for example, ethylene) and oxygen gas to produce an oxygen-containing compound (for example, acetic acid) is not particularly limited. The reaction temperature is preferably from 100 to 300° C., more preferably from 120 to 250° C. The reaction pressure is not particularly limited but in view of equipment, a pressure of 0.0 MPa (gauge pressure) to 3.0 MPa (gauge pressure) is advantageous in practice. The reaction pressure is more preferably from 0.1 MPa (gauge pressure) to 1.5 MPa (gauge pressure).

In the production process of oxygen-containing gas of the present invention (III), the gas supplied to the reaction system contains a raw material olefin (e.g., ethylene) and oxygen gas, and, if desired, nitrogen, carbon dioxide, rare gas or the like may be further used as the diluent.

The raw material olefin such as ethylene is supplied to the reaction system in such an amount as to occupy 5 to 80 vol %, preferably from 8 to 60 vol %, and the oxygen is supplied in such an amount as to occupy 1 to 15 vol %, preferably from 3 to 12 vol %, based on the entire amount of the supply gas.

In this reaction system, when water is present within the reaction system, a remarkable effect is brought out on the enhancement of activity and selectivity for the production of an oxygen-containing compound such as acetic acid as well as on the maintenance of activity of the catalyst. In the reaction gas, the water vapor is suitably contained in an amount of 1 to 50 vol %, preferably from 5 to 40 vol %.

In the process for producing an oxygen-containing compound such as acetic acid of the present invention (III), the raw material olefin (for example, ethylene) is preferably a high-purity olefin, but another gas (for example, a lower saturated hydrocarbon such as methane, ethane and propane) may be mixed in the olefin. The oxygen may be supplied in the form of an oxygen diluted with an inert gas such as nitrogen or carbonic acid gas, for example, in the form of an air, but in the case of circulating the reaction gas, it is generally advantageous to use an oxygen gas in a high concentration, preferably in a concentration of 99% or more.

(Reaction Conditions)

The reaction mixed gas is preferably passed to the catalyst, in the standard state, at an SV of 10 to 15,000 hr$^{-1}$, more preferably from 300 to 8,000 hr$^{-1}$.

The reaction style is not particularly limited and a known method such as fixed bed or fluidized bed can be employed. Use of a fixed bed where the above-described catalyst is packed in a reaction tube having corrosion resistance is preferred and practically advantageous.

EXAMPLES

The present invention is described in greater detail below by referring to Examples and Comparative Examples, but the present invention is not limited thereto.

[Use of Water]

In all Examples, the water used was deionized water.

Example 1

Zirconium hydroxide [$Zr(OH)_4$, produced by Daiichi Kigenso Kagaku Kogyo Co., Ltd.] was dipped in an aqueous solution of ammonium metatungstate [$(NH_4)_{10}W_{12}O_{41} \cdot 5H_2O$, produced by Wako Pure Chemical Industries, Ltd.] to give a W/Zr molar ratio of 0.1, dry-solidified by evaporation, further dried at 100° C. for one day and night in air, and then fired at 800° C. for 3 hours in air to obtain tungsten-zirconium ($W_aZrO_y$).

Subsequently, an HCl aqueous solution of palladium chloride [$PdCl_2 \cdot H_2O$, produced by Wako Pure Chemical Industries, Ltd.] was weighed to give a proportion of 1 part in terms of palladium element based on 100 parts of $W_aZrO_y$ obtained above. Thereafter, $W_aZrO_y$ was dipped in this solution, dry-solidified by evaporation and then fired at 400° C. for 5 hours in air to obtain Catalyst 1 for Production of Acetic Acid.

Examples 2 to 5

These Examples were performed in the same manner as Example 1 except that the W/Zr molar ratio was changed to a value shown in "Table 1" below.

TABLE 1

| Example | Catalyst for Production of Acetic Acid | W/Zr Molar Ratio | Mass parts of Pd to 100 parts of $W_aZrO_y$ |
|---|---|---|---|
| Example 1 | 1 | 0.1 | 1.0 |
| Example 2 | 2 | 0.2 | 1.0 |
| Example 3 | 3 | 0.3 | 1.0 |
| Example 4 | 4 | 0.4 | 1.0 |
| Example 5 | 5 | 0.5 | 1.0 |

Examples 6 to 8

These Examples were performed in the same manner as Example 1 except that the mass ratio of Pd to $W_aZrO_y$ was changed to a value shown in "Table 2" below.

TABLE 2

| Example | Catalyst for Production of Acetic Acid | Mass Parts of Pd to $W_aZrO_y$ 100 parts |
|---|---|---|
| Example 6 | 6 | 0.5 |
| Example 7 | 7 | 1.5 |
| Example 8 | 8 | 2.0 |

Comparative Example 1

An HCl aqueous solution of palladium chloride was dipped in 100 parts of zirconium hydroxide to give a proportion of 1.0 part, dry-solidified by evaporation and then dried at 400° C. for 5 hours in air to obtain Catalyst 9 for Production of Acetic Acid.

Comparative Example 2

Zirconium hydroxide was dipped in an aqueous solution of ammonium metatungstate to give a W/Zr molar ratio of 0.1, dry-solidified by evaporation, further dried at 100° C. for one day and night in air and then fired at 800° C. for 3 hours in air to obtain Catalyst 10 for Production of Acetic Acid.

Comparative Example 3

A catalyst comprising palladium and heteropolyacid was produced according to Example 1 of Kokai No. 7-89896.

A silica support (250 ml) was dipped in an aqueous solution containing 10 g of sodium tetrachloropalladate [Na$_2$PdCl$_4$, produced by Tanaka Kikinzoku Kogyo K.K.], allowed to absorb the entire amount, added in 200 ml of an aqueous solution containing sodium metasilicate 18 g and then left standing for 20 hours. Thereafter, 10 ml of an aqueous 85% hydrazine solution was added thereto to reduce the sodium chloropalladate into metal palladium. The resulting support containing metal palladium was washed with water, dried at 110° C. for 4 hours, charged into 90 ml of an aqueous solution containing 20 parts of silicotungstic acid based on the support 100 parts, allowed to absorb the entire solution, and then dried at 110° C. for 4 hours to obtain Catalyst 11 for Production of Acetic Acid.

Examples 9 to 16 and Comparative Examples 4 to 6

Catalysts 1 to 89 for Production of Acetic Acid obtained in Examples 1 to 89 and Catalysts 9 to 11 for Production of Acetic Acid obtained in Comparative Examples 1 to 3 each in 2 ml was packed in an SUS316-made reaction tube (inner diameter: 10 mm) and for the reduction of palladium chloride pretreatment, a mixed gas of hydrogen:helium=1:1 was passed at 300° C. and 60 ml/min for 1 hour.

Subsequently, a gas obtained by mixing ethylene oxygen gas:vapor water:nitrogen gas at a volume ratio of 50:7:30:13 was introduced at a space velocity of 3,000 hr$^{-1}$ under the conditions such that the reaction temperature of the catalyst layer was 150° C. and the reaction pressure was 0.4 MPaG (gauge pressure), thereby performing a reaction of obtaining acetic acid from ethylene and oxygen.

With respect to the analysis method in the reaction, the entire amount of the outlet gas passed through the catalyst-packed layer was cooled and as for the condensed and collected reaction solution, the entire amount was recovered and analyzed by gas chromatography. As for the uncondensed gas remaining without being condensed, the entire amount of the uncondensed gas flowed out within the sampling time was measured and by taking out a part thereof, the composition was analyzed by gas chromatography.

The ethylene oxidation reaction was performed by using each catalyst. The results are shown in Table 3.

The results of each reaction product were evaluated by the following formulae:

Conversion (%)=((mol number of supplied raw material)−(mol number of unreacted raw material))/ (mol number of supplied raw material)×100   (1)

Selectivity (%)=((mol number of each reaction product)×(carbon number of each reaction product)/ (carbon number of supplied ethylene))/(mol number of reacted ethylene)×100   (2)

STY of acetic acid (g/hL)=(mol number of acetic acid per hour)/(catalyst volume (L))   (3)

TABLE 3

Results of Ethylene Oxidation Reaction

| Catalyst for Production of Acetic Acid | | Conversion, % | | Selectivity, % | | | | | STY of Acetic Acid, g/hL |
|---|---|---|---|---|---|---|---|---|---|
| | | Ethylene | Oxygen | Acetic Acid | Acetaldehyde | Ethanol | CO$_2$ | CO | |
| Example 9 | 1 | 1.1 | 20.6 | 76.2 | 1.6 | 0 | 21.5 | 0.7 | 32.2 |
| Example 10 | 2 | 1.7 | 24.8 | 79.7 | 0.8 | 0 | 19.0 | 0.5 | 51.9 |
| Example 11 | 3 | 1.7 | 22.7 | 79.7 | 0.8 | 0 | 19.1 | 0.4 | 51.1 |
| Example 12 | 4 | 1.5 | 22.4 | 71.8 | 0.6 | 0 | 27.0 | 0.6 | 41.2 |
| Example 13 | 5 | 1.2 | 17.1 | 74.1 | 0.9 | 0 | 24.6 | 0.3 | 34.5 |
| Example 14 | 6 | 0.5 | 9.3 | 75.1 | 1.5 | 0 | 23.4 | 0.0 | 54.0 |
| Example 15 | 7 | 1.4 | 21.7 | 77.3 | 0.8 | 0 | 21.3 | 0.6 | 48.0 |
| Example 16 | 8 | 1.7 | 24.8 | 79.7 | 0.8 | 0 | 19.0 | 0.5 | 51.9 |
| Comparative Example 4 | 9 | 0.1 | 4.2 | 57.9 | 3.5 | 0 | 38.6 | 0.0 | 2.4 |
| Comparative Example 5 | 10 | 0.1 | 0.2 | 0 | 23 | 73 | 2.3 | 0.0 | 0.0 |
| Comparative Example 6 | 11 | 1.1 | 18.7 | 52.8 | 0.9 | 0.4 | 45.9 | 0.0 | 22.1 |

INDUSTRIAL APPLICABILITY

As described hereinabove, by using the catalyst of the present invention (I), an oxygen-containing compound can be produced from an olefin and oxygen with high productivity and high selectivity.

The invention claimed is:

1. A process for producing an oxygen-containing compound, comprising reacting an olefin and oxygen in a gas phase in the presence of a catalyst, wherein the olefin is propylene, the oxygen-containing compound is at least one compound selected from acetone, propionaldehyde, propionic acid and acetic acid; and the catalyst is represented by the following formula:

Pd/W$_a$ZrO$_x$ wherein Pd is a palladium-containing compound, a is a W/Zr molar ratio of from 0.01 to 5.0, and x is a value defined by the oxidized state of tungsten (W), zirconium (Zr) and palladium (Pd), and wherein the content of palladium element in the catalyst is from 0.001 to 15 parts by mass based on 100 parts by mass of $W_aZrO_x$.

2. A process for producing acetic acid, comprising reacting ethylene and oxygen in a gas phase in the presence of a catalyst represented by the following formula:

$$Pd/W_aZrO_x$$

wherein Pd is a palladium-containing compound, a is a W/Zr molar ratio of from 0.01 to 5.0, and x is a value defined by the oxidized state of tungsten (W), zirconium (Zr) and palladium (Pd), and wherein the content of palladium element in the catalyst is from 0.001 to 15 parts by mass based on 100 parts by mass of $W_aZrO_x$.

3. The process according to claim 2, wherein the catalyst is produced by a process comprising the following first and second steps:
   First Step:
   a step of causing a tungsten compound and a zirconium compound to coexist and heat-treating these compounds to produce a compound represented by the following formula:

$$W_aZrO_y$$

wherein a is a W/Zr molar ratio, and y is a value defined by the oxidized state of tungsten (W), and zirconium (Zr);

Second Step:
   a step of loading palladium compound on the compound $W_aZrO_y$ obtained in the first step to obtain a catalyst for the production of an oxygen-containing compound.

4. The process according to claim 3, wherein in said first step, the heat-treatment temperature is from 400 to 1,200° C.

5. A process for producing an oxygen-containing compound, comprising reacting an olefin and oxygen in a gas phase in the presence of a catalyst, wherein the olefin is at least one member selected from 1-butene, cis-2-butene and trans-2-butene, the oxygen-containing compound is at least one compound selected from methyl ethyl ketone, n-butylaldehyde, butyric acid, propionaldehyde, propionic acid, acetaldehyde and acetic acid, and the catalyst is represented by the following formula:

$$Pd/W_aZrO_x$$

wherein Pd is a palladium-containing compound, a is a W/Zr molar ratio of from 0.01 to 5.0, and x is a value defined by the oxidized state of tungsten (W), zirconium (Zr) and palladium (Pd), and wherein the content of palladium element in the catalyst is from 0.001 to 15 parts by mass based on 100 parts by mass of $W_aZrO_x$.

* * * * *